United States Patent [19]

Wagner et al.

[11] 4,103,029

[45] Jul. 25, 1978

[54] AMINO SUBSTITUTED ARYLTHIO-ALKANOIC ACIDS HAVING HYPOLIPIDEMIC ACTIVITY

[75] Inventors: Eugene R. Wagner, Midland; Bobbie J. Allen, Detroit, both of Mich.

[73] Assignee: The Dow Chemical Company, Midland, Mich.

[21] Appl. No.: 823,298

[22] Filed: Aug. 10, 1977

Related U.S. Application Data

[62] Division of Ser. No. 671,909, Mar. 29, 1976, Pat. No. 4,062,975.

[51] Int. Cl.$^2$ .................... A61K 31/20; C07C 149/43
[52] U.S. Cl. ................................. 424/318; 260/402.5
[58] Field of Search ................ 424/318, 319; 260/516, 260/402.5

[56] References Cited

U.S. PATENT DOCUMENTS

| | | | |
|---|---|---|---|
| 2,681,363 | 6/1954 | Schwenk et al. | 424/317 X |
| 3,369,025 | 2/1968 | Bolhofer | 424/263 X |
| 3,383,411 | 5/1968 | Schultz et al. | 260/521 R |
| 3,652,646 | 3/1972 | Leigh et al. | 424/308 X |
| 3,707,549 | 12/1972 | Mills | 424/308 X |
| 3,843,662 | 10/1974 | Holland | 424/319 X |
| 3,855,285 | 12/1974 | Holland | 424/319 X |

FOREIGN PATENT DOCUMENTS

| | | |
|---|---|---|
| 815,703 | 5/1974 | Belgium. |
| 7,333,742 | 10/1970 | Japan. |
| 7,333,743 | 10/1970 | Japan. |

OTHER PUBLICATIONS

Metz et al.; vol. 82, 43070h (1975).
Kuroda et al.; vol. 80, 133072y (1974).
Kuroda et al.; vol. 80, 133073z (1974).

*Primary Examiner*—Allen J. Robinson
*Attorney, Agent, or Firm*—James W. Ambrosius

[57] ABSTRACT

This invention relates to novel compounds and compositions of amino substituted arylthio-alkanoic acid, the corresponding pharmaceutically-acceptable salts and the esters thereof. The invention also relates to methods for reducing plasma lipid levels in animals using the compounds of the present invention.

4 Claims, No Drawings

AMINO SUBSTITUTED ARYLTHIO-ALKANOIC ACIDS HAVING HYPOLIPIDEMIC ACTIVITY

This is a division of application Ser. No. 671,909 filed Mar. 29, 1976, now U.S. Pat. No. 4,062,9750.

BACKGROUND OF THE INVENTION

As established by various studies, it is recognized that cholesterol and triglycerides play a major role in the formation of artherosclerotic plaques by accelerating the deposition of blood lipids in the arterial wall.

Arylthio-alkanoic acids and various derivatives thereof have been reported as having hypolipidemic activity in U.S. Pat. Nos. 3,652,646; 3,369,025; and 3,707,549. Other hypolipidemic agents and compounds intended for use in the treatment of heart disease which have a structure less closely related to the compounds of the present invention are reported in U.S. Pat. Nos. 3,843,662 and 3,855,285; CA82:43070h (German. Offen. 2,316,914); Belgian Pat. 815,703; Japanese Pat. Nos. 7,333,742 and 7,333,743; and CA80:133072y and 133073z.

Other references of interest are U.S. Pat. Nos. 2,681,363 and 3,383,411.

SUMMARY OF THE INVENTION

The present invention relates to amino substituted arylthio-alkanoic acids, compositions containing these compounds, the corresponding pharmaceutically-acceptable salts and the esters thereof. The invention also relates to methods for reducing plasma lipid levels in animals using the compounds or compositions of the present invention.

The compounds of the present invention and the corresponding esters thereof are represented by the general formula:

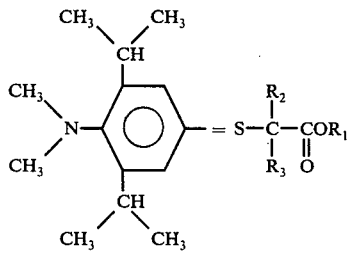

wherein
$R_1$ represents hydrogen or a lower alkyl having from 1 to about 5 carbon atoms. And $R_2$ and $R_3$ independently represent hydrogen or an alkyl having from 1 to about 10 carbon atoms.

Pharmaceutically-acceptable salts of the arylthio-alkanoic acids, i.e. when $R_1$ is hydrogen, are considered as being within the scope of this invention. Pharmaceutically-acceptable salts refer to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compound may be obtained by treating the corresponding sodium salt with an appropriate aluminum complex such as aluminum chloride hexahydrate etc.

The compounds employed in the compositions and methods of the present invention are crystalline solids which are soluble in many common organic solvents such as, for example, acetone, benzene, alcohols, and lower alkanes.

Compounds of the present invention have shown hypolipidemic activity in animals and in particular in mammals. Hypolipidemic activity as used herein refers to the effect of lowering the blood lipid content and in particular the cholesterol and triglyceride content of the serum. The compounds of the present invention are therefore suitable for use in treating serum hyperlipidemia in mammals and in particular are useful for the treatment of hypercholesterolemia and hypertriglyceridemia, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The hypolipidemic amount of the arylthio-alkanoic acid compounds to be administered to an animal, that is the amount which is effective to significantly lower the serum lipid level, can vary depending upon such factors as the animal treated, the particular arylthio-alkanoic acid compound employed, the desired lipid level to be obtained whether or not the animal is hyperlipidemic, the period of administration and the method of administration. In general an effective daily dosage range is from about 1 mg/kg of body weight to 400 mg/kg of body weight, with a daily dosage range of from about 5 mg/kg to 30 mg/kg of body weight being preferred.

For oral administration, pharmaceutical preparations of the arylthio-alkanoic acids may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or cod liver oil can be used.

Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The arylthio-alkanoic acids can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

DETAILED DESCRIPTION OF THE INVENTION

The amino substituted arylthio-alkanoic acid compounds that are the subject of the present invention in general are prepared by a four step reaction. In the first step 2,6-di-isopropylaniline is reacted with a thiocyanate salt such as ammonium or sodium thiocyanate to yield the substituted phenylthiocyanate. In the second step the 4-amino-3,5-di-isopropylphenylthiocyanate prepared in the first step is methylated using methyl iodide. In the third step the phenylthiocyanate is reduced to the corresponding mercaptophenol using lithium aluminum hydride. In the final step the mercaptophenol is reacted with a pre-selected halo substituted alkanoic acid to give the desired amino substituted arylthio-alkanoic acid. It has been found that the isopropylaniline must be converted to the thiocyanate before the methylation of the amino groups. The following references are of interest N. I. Kudryashova and N. V. Khromov-Borisov, CA. 56:3383a and Org. Syn. II, p 574.

The above steps may be represented as follows:

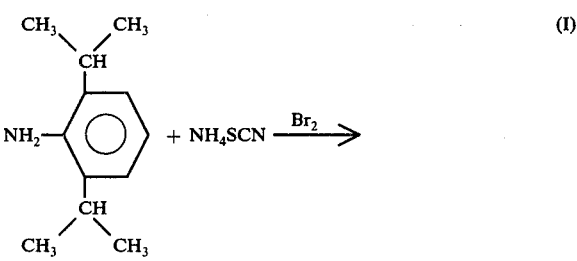

(I)

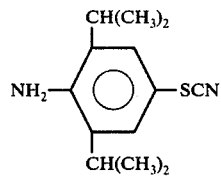

(II)

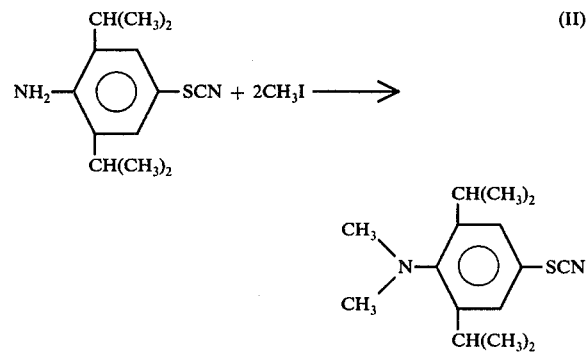

(III)

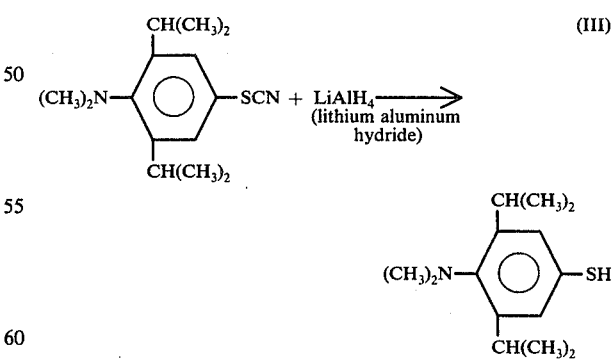

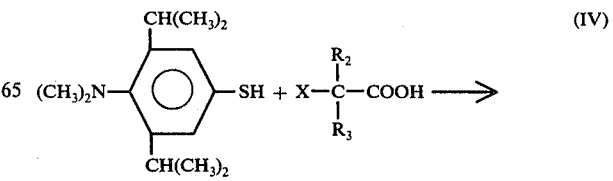

(IV)

-continued

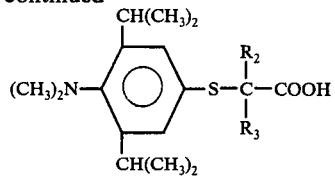

wherein X is a halogen and $R_2$ and $R_3$ independently represent hydrogen or an alkyl having from 1 to about 10 carbon atoms.

In the preparation of the esters of the arylthio-alkanoic acids, i.e. where $R_1$ is a lower alkyl of from 1 to 5 carbon atoms the ester of the alkanoic acid is reacted with the mercaptophenol instead of the alkanoic acid. Alternately the arylthio-alkanoic acid could be reacted with the appropriate alcohol to yield the ester.

The following example represents the preparation of a specific embodiment of the present invention but is not to be construed as a limitation thereon.

EXAMPLE 1

Preparation of 2-((4-(dimethylamino)-3,5-bis(1-methylethyl)phenyl)thio)-hexanoic acid A stirred mixture of 29.2 grams of 2,6-di-isopropylaniline and 33.4 grams of sodium thiocyanate in 225 ml. of glacial acetic acid was cooled to 10° C and a solution of 40 grams of bromine in 40 ml of acetic acid was added dropwise. When about half of the bromine had been added the reaction mass become very thick with precipitate. The addition was continued at a faster rate and the temperature was allowed to rise between 15 and 20° C. Near the end of the addition the mixture became very thick, and it was necessary to stir by hand. The reaction mass was allowed to stand for two hours. The reaction mass was poured into 2 liters of water, stirred until it crystallized, and then filtered. The solid was washed with water and dried in air. The crude thiocyanate intermediate was extracted from the residue with 1500 ml. of boiling hexane in two portions. The filtered hexane was concentrated in 400 ml., refiltered and concentrated further to 200 ml. and allowed to cool. Crystals formed, and after cooling were harvested, washed with hexane and dried to give 25.5 grams of the thiocycanate intermediate. The melting point was 86°–87° C. IR data confirmed the desired structure.

A mixture of 23.5 grams of 4-amino-3,5-di-isopropylphenylthiocyanate prepared above, 12 grams of calcium carbonate, 30 grams of methyl iodide and 20 ml. of water in 100 ml. of methanol was stirred at gentle reflux for 18 hours. The reaction mass was filtered and the solvent evaporated to leave a two phase yellow oil. The residue was treated with 20% NaOH and benzene, and then filtered. The filtrate layers were separated, and the organic layer was washed three times with water, dried over sodium sulfate ($Na_2SO_4$) and evaporated to leave 27.6 grams of a yellow oil. This was chromatographed on 30 grams Baker 60-200 mesh silica gel with chloroform ($CHCl_3$). The first 250 ml fractions contained a yellow oil which crystallized on scratching. 12.8 Grams of the methylated intermediate, 4-dimethylamino-3,5-di-isopropylphenylthiocyanate, was obtained upon recrystallization from 250 ml. of ethanol that had been diluted with water to the point of cloudiness. The melting point was 55°–56° C. NMR and infrared analysis confirmed the structure. More material could be obtained by chromotagraphy of the mother liquids.

To a stirred suspension of 2 grams of lithium aluminum hydride in 250 ml of tetrahydrofuran a solution containing 10 grams of the methylated thiocyanate prepared above in 50 ml. of tetrahydrofuran was added dropwise over a period of 1 hour. The reaction mass was heated at reflux for 2 hours with stirring. The lithium aluminum hydride was destroyed with isopropyl alcohol. A saturated sodium chloride solution was added until a clear layer separated. The cooled reaction mass was filtered and the organic solvents stripped off. The mercaptophenol was extracted into 300 ml of toluene and this was washed and dried over sodium sulfate and concentrated to 100 ml. of volume and cooled.

To the toluene solution containing the mercaptophenol prepared above 200 ml. of 20% sodium hydroxide and 7.4 grams of 2-bromo-hexanoic acid were added. The reaction mass was stirred at room temperature for about one hour. The mixture was then treated with 100 ml. of 1 N hydrochloric acid. The resulting layers were separated and the toluene was washed twice or until neutral. The organic layers were dried over $Na_2SO_4$ and evaporated to leave a light yellow oil weighing 13.4 grams which crystallized on standing. The crystals of 2-((4-(di-methylamino)-3,5-bis(1-methylethyl)phenyl)thio)-hexanoic acid were washed with cold pentane and sucked dry on a suction filter to give 3.14 grams of product. The melting point was found to be 66°–68° C. Infrared and NMR analysis confirmed the structure.

Following the general procedure set forth in the preceding example a number of other amino substituted arylthio-alkanoic acids as shown in Table I were prepared having the general formula:

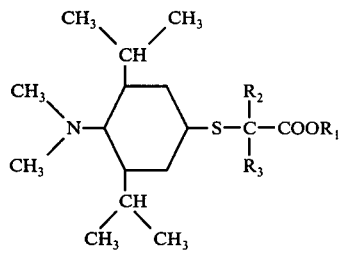

Table I

| Ex. No. | $R_3$ | $R_2$ | $R_1$ | Melting point or boiling point at mm Hg |
|---|---|---|---|---|
| 2 | $(CH_2)_2CH_3$ | H | H | B.P. 190–195° C at 0.8mm |
| 3 | $CH_2CH_3$ | H | H | — |
| 4 | $(CH_2)_9CH_3$ | H | H | — |
| 5 | H | H | H | 106–107° C |
| 6 | $CH_3$ | H | H | — |
| 7 | $CH_3$ | $CH_2CH_3$ | $CH_2CH_3$ | B.P. 155–160° C at 0.8mm |
| 8 | $CH_3$ | $CH_2CH_3$ | H | 128–130° C |
| 9 | $CH(CH_3)_2$ | H | $CH_2CH_3$ | B.P. 160–165° C at 0.3mm |
| 10 | $CH_3$ | $CH_3$ | H | 156–158° C |
| 11 | $CH(CH_3)_2$ | H | H | 175–177° C |
| 12 | $(CH_2)_4CH_3$ | H | $CH_2CH_3$ | B.P. 174°at 1mm |
| 13 | $(CH_2)_4CH_3$ | H | H | — |

The hypolipidemic effect of the representative active compounds employed in the practice of the invention is illustratively demonstrated in rats. In this procedure, an active compound as disclosed herein is dissolved in acetone, taken up on a silica gel and mixed with normal ground feed to yield concentrations of 0.125 percent of the compound in the animal feed. The treated feed was administered to male rats weighing 150–160 grams over a fourteen day period. Following the fourteen day feeding period, the rats were sacrificed, and blood samples were collected. The liver was removed, weighed, and frozen for future analysis. The relative levels of serum cholesterol in the blood samples were determined by the Henly method. A. A. Henly, Analyst, 82, 286 (1957). Liver cholesterol was measured by the Sperry-Webb method. Journal of Biological Chemistry 187,97 (1950). The relative levels of triglycerides in the blood and liver samples were determined by the Van Handel and Zilversmit method. J. Lab. Clin. Med. 50, 152 (1957) and Clin. Chem. 7, 249 (1961). Taking the average levels of the control rats as standard, the mean results obtained in the treated groups is thereby ascertained.

The data presented in Table II summarize the results of the above studies.

Table II

| Compound Example Number | Serum Cholesterol* % reduction | Serum Triglycerides* % reduction | Liver Cholesterol* | Liver Triglycerides* | Liver weight* % change |
| --- | --- | --- | --- | --- | --- |
| 1 | −17 | −70 | +20 | +59 | — |
| 2 | −21 | −65 | −4 | +14 | +23 |
| 3 | −11 | −73 | −9 | +65 | +32 |
| 4 | −14 | −35 | +13 | +35 | −7 |
| 5 | −11 | −50 | — | — | +49 |
| 6 | −17 | −67 | — | — | +63 |
| 7 | −8 | −67 | — | — | +53 |
| 8 | −8 | −63 | — | — | +82 |
| 9 | −14 | −43 | — | — | +29 |
| 10 | −9 | −70 | — | — | +66 |
| 11 | −26 | −49 | −24 | −15 | +17 |
| 12 | −20 | −22 | +6 | +51 | 30 7 |
| 13 | −18 | −45 | +11 | +60 | 0 |

*All data represent relative change in values for the treated animals when compared to the control group.

The data indicates that the compounds that are the subject of the present invention significantly reduced both serum cholesterol and serum triglycerides. In several examples this reduction was accomplished without extreme changes in liver weight. Note, for example, the compound of Example 13 which reduced serum cholesterol by 18%, serum triglycerides by 45% and produced no change in liver weight. The compounds of Example 2, 2-((4-(dimethylamino)-3,5-bis(1-methylethyl)phenyl)-thio)-pentanoic acid, and Example 11, 2-((4-dimethylamino)-3,5-bis(1-methylethyl)-phenyl)thio)-3-methylbutanoic acid, show good hypolipidemic activity while not causing unreasonable enlargement of the liver.

I claim:

1. A compound of the formula

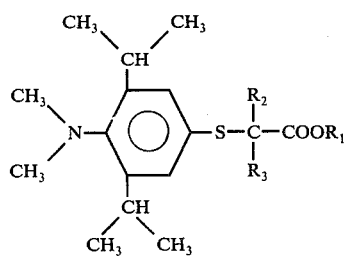

wherein $R_1$ represents hydrogen and $R_2$ and $R_3$ independently represent hydrogen or an alkyl having from 6 to about 10 carbon atoms with the proviso that both $R_2$ and $R_3$ cannot be hydrogen and the pharmaceutically acceptable salts thereof.

2. A hypolipidemic composition comprising a suitable pharmaceutical carrier and a hypolidemically effective amount of a compound having the formula

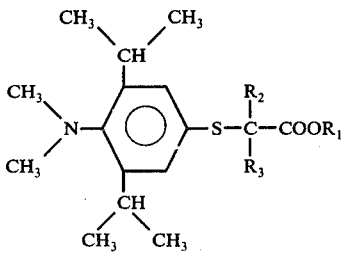

wherein $R_1$ represent hydrogen and $R_2$ and $R_3$ independently represent hydrogen or an alkyl having from 6 to about 10 carbon atoms with the proviso that both $R_2$ and $R_3$ cannot be hydrogen and the pharmaceutically acceptable salts thereof.

3. A method for lowering elevated serum lipids in a mammal which comprises administering internally to the mammal a hypolipidemically effective amount of a compound having the formula

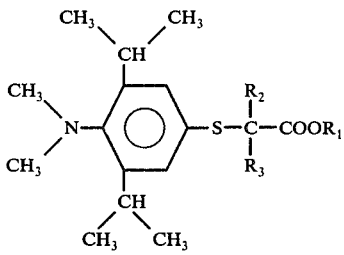

wherein $R_1$ represents hydrogen and $R_2$ and $R_3$ independently represent hydrogen or an alkyl having from 6 to about 10 carbon atoms with the proviso that both $R_2$ and $R_3$ cannot be hydrogen and the pharmaceutically acceptable salts thereof.

4. The method of claim 3 wherein the mammal is administered 5 mg/kg body weight to 30 mg/kg body weight of the compound.

* * * * *

UNITED STATES PATENT AND TRADEMARK OFFICE
CERTIFICATE OF CORRECTION

PATENT NO. : 4,103,029

DATED : July 25, 1978

INVENTOR(S) : Eugene R. Wagner, et al.

It is certified that error appears in the above-identified patent and that said Letters Patent are hereby corrected as shown below:

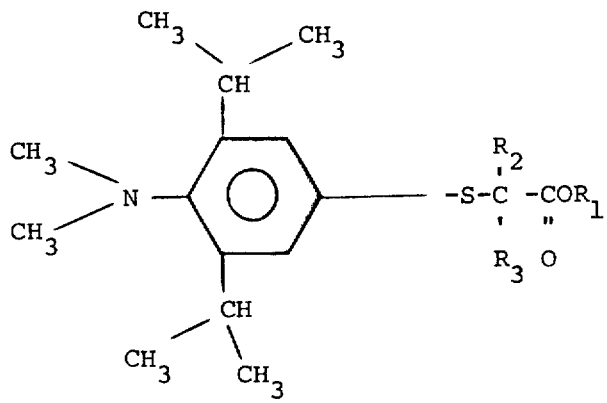

Column 1, between lines 35 and 45, FORMULA should read as written above;

Column 5, line 31, "become" should read -- became --;

Column 5, line 42, "in" should read -- to --;

Column 6, lines 40-45, insert circle in benzene ring;

Column 6, line 57, please move "at 0.8mm" to Column 5 of TABLE I under "B.P. 155-160°C";

Column 6, line 61, last line of last column in TABLE I, please insert -- C -- after "174°";

UNITED STATES PATENT AND TRADEMARK OFFICE
CERTIFICATE OF CORRECTION

PATENT NO. : 4,103,029
DATED : July 25, 1978
INVENTOR(S) : Eugene R. Wagner, et al.

It is certified that error appears in the above-identified patent and that said Letters Patent are hereby corrected as shown below:

Column 8, TABLE II, under last column, compound example No. 12, please change "30 7" to read -- +7 --;

Signed and Sealed this

Seventeenth Day of April 1979

[SEAL]

Attest:

RUTH C. MASON
Attesting Officer

DONALD W. BANNER
Commissioner of Patents and Trademarks